US009459225B2

(12) United States Patent
Kivijarvi et al.

(10) Patent No.: US 9,459,225 B2
(45) Date of Patent: Oct. 4, 2016

(54) MOISTURE METER FOR DETERMINING THE MOISTURE CONTENT OF PARTICULATE MATERIAL

(71) Applicant: Farmcomp Oy, Tuusula (FI)

(72) Inventors: Janne Kivijarvi, Espoo (FI); Jere Keskiaho, Vantaa (FI); Johannes Hyrsky, Espoo (FI)

(73) Assignee: Farmcomp Oy, Tuusula (FI)

( * ) Notice: Subject to any disclaimer, the term of this patent is extended or adjusted under 35 U.S.C. 154(b) by 380 days.

(21) Appl. No.: 13/832,264

(22) Filed: Mar. 15, 2013

(65) Prior Publication Data

US 2014/0210492 A1 Jul. 31, 2014

(30) Foreign Application Priority Data

Jan. 29, 2013 (FI) .................................... 20135083

(51) Int. Cl.
*G01N 19/10* (2006.01)
*G01N 27/22* (2006.01)

(52) U.S. Cl.
CPC ............ *G01N 27/223* (2013.01); *G01N 19/10* (2013.01); *G01N 27/226* (2013.01)

(58) Field of Classification Search
CPC .................................................. G01N 27/223
USPC .............................................................. 73/73
See application file for complete search history.

(56) References Cited

U.S. PATENT DOCUMENTS

| 2,054,476 | A | * | 9/1936 | Derry ...................... B29C 33/72 100/102 |
| 4,107,599 | A | * | 8/1978 | Preikschat .................... 324/689 |
| 4,121,151 | A | * | 10/1978 | Funk .................... G01N 27/223 324/659 |
| 4,193,116 | A | | 3/1980 | Funk |
| 5,126,679 | A | * | 6/1992 | Spry ........................ G01N 33/10 324/692 |
| 5,253,512 | A | * | 10/1993 | Le Gigan ................ G01N 33/10 374/142 |

(Continued)

FOREIGN PATENT DOCUMENTS

| IL | WO 0014552 A1 * | 3/2000 | ............. G01N 22/04 |
| WO | 85/00427 | 1/1985 | |
| WO | WO 2011036342 A1 | 3/2011 | |

OTHER PUBLICATIONS

Office Action and Search Report from the National Board of Patents and Registration of Finland relating to Finnish Patent Application No. 20135083 dated Sep. 26, 2013.

(Continued)

*Primary Examiner* — Robert Huber
*Assistant Examiner* — Herbert K Roberts
(74) *Attorney, Agent, or Firm* — Calfee, Halter & Griswold LLP (57) ABSTRACT

A moisture meter for determining the moisture content of particulate material is provided. The moisture meter comprises a frame part, a space, a measuring cup disposed within said space for receiving a sample of the particulate material which moisture is to be measured, and moisture measuring means. The moisture meter comprises a swiping means for removing at least partly a part of a sample of particulate material which moisture is to be measured, which part of the sample of particulate material extends out of the inner space of the measuring cup through the open end of the measuring cup. The swiping means are movably attached to the frame part for movement in a swiping path where a swiping member of the swiping means is configured to move essentially along the open end of the measuring cup.

20 Claims, 6 Drawing Sheets

(56) References Cited

U.S. PATENT DOCUMENTS

| | | | | |
|---|---|---|---|---|
| 5,767,685 A | * | 6/1998 | Walker | G01N 22/04 324/632 |
| 2003/0033862 A1 | * | 2/2003 | McElhaney | G01N 27/223 73/73 |
| 2004/0189284 A1 | * | 9/2004 | Haubold | F15B 15/10 324/207.2 |
| 2006/0013279 A1 | | 1/2006 | Funk | |
| 2011/0086684 A1 | * | 4/2011 | Luellen | G01N 1/04 460/79 |

OTHER PUBLICATIONS

Office Action from the Finnish Patent and Registration Office relating to Finnish Patent Application No. 20135083 dated Feb. 9, 2015.

* cited by examiner

MOISTURE METER FOR DETERMINING THE MOISTURE CONTENT OF PARTICULATE MATERIAL

RELATED APPLICATIONS

The present application claims the benefit of Finland Patent Application Number 20135083, filed on Jan. 29, 2013, which is fully incorporated herein by reference.

TECHNICAL FIELD

The invention relates to a moisture meter for determining the moisture content of particulate material. By particulate material is meant for example, but not excluding other particulate materials, grain in ungrounded state and in ground state.

Electrical moisture measuring methods employed most frequently in measuring the moisture content of granular material are based either on measurement of resistance in which the effect of moisture on the resistance of the material being examined is observed, on measurement of capacitance in which the moisture alters the dielectric constant and consequently the capacitance of the pick-up, or on impedance measurement in which the effect of moisture both on the resistance and the capacitance of the pick-up is observed.

In all said measuring modes a sample must be used, in order to gain an accurate moisture content figure for the material under examination, which prior to the measuring event has been brought into a given state, which must be repeatable at different times of measuring. This may be done e.g. by measurement of bulk density, or by pressing the sample against the measuring electrodes with a known force.

Publication WO 85/00427 presents a moisture meter.

BACKGROUND OF THE INVENTION

The object of the invention is to provide an improved moisture meter which is capable of repeatably providing a standardized sample of particulate material having essentially the same volume.

SUMMARY

The moisture meter comprises a swiping means for removing at least partly a part of a sample of particulate material whose moisture is to be measured and which has been poured into the inner space of a measuring cup through the open end of the measuring cup, which part of the sample of particulate material extends out of the inner space of the measuring cup through the open end of the measuring cup. The swiping means being movably attached to a frame part for movement in a swiping path where a swiping member of the swiping means is configured to move essentially along the open end of the measuring cup.

The volume of the inner space of the measuring cup can be considered to be defined by a bottom wall, a cylindrical side wall and an imaginary top wall at the open end of the measuring cup. The swiping means is movably attached to the frame part for movement in a swiping path where a swiping member of the swiping means is configured to move essentially along an imaginary top wall at the open end of the measuring cup so that the volume of the sample will have essentially the volume of the measuring cup.

BRIEF DESCRIPTION OF THE DRAWINGS

These and other features and advantages of the present invention will become better understood with regard to the following written description and the following drawings.

DETAILED DESCRIPTION

The Figures show a moisture meter for determining the moisture content of particulate material. The moisture meter comprises a frame part 1. The moisture meter comprises a space 2 defined by said frame part 1.

The moisture meter comprises a measuring cup 3 disposed within said space 2 for receiving a sample of the particulate material (not shown in the drawings) whose moisture is to be measured, wherein measuring cup 3 has an open end 4 through which particulate material whose moisture is to be measured is to be poured and an inner space 5 having a given volume.

The moisture meter comprises moisture measuring means for measuring the moisture content of a sample of the particulate material received in the measuring cup 3.

Said moisture measuring means for measuring the moisture content of a sample of the particulate material received in the measuring cup 3 may, as known to those skilled in the art, be formed so that in said moisture meter said measuring cup 3 being a capacitor of which the impedance is proportional to the moisture content and quantity of a sample of the particulate material received in the measuring cup 3. Alternatively the moisture measuring means may for example be optical moisture measuring means for measuring the moisture content of a sample of the particulate material received in the measuring cup 3.

The moisture meter comprises a swiping means 9 for removing at least partly a part of a sample of particulate material whose moisture is to be measured and which has been poured into the inner space of the measuring cup 3 through the open end of the measuring cup 3, which part of the sample of particulate material extends out of the inner space of the measuring cup 3 through the open end of the measuring cup 3. The swiping means 9 being movably attached to the frame part 1 for movement in a swiping path where a swiping member 10 of the swiping means 9 is configured to move essentially along the open end of the measuring cup 3.

The volume of the inner space of the measuring cup 3 can be considered to be defined by a bottom wall 6, a cylindrical side wall 7 and an imaginary top wall 8 at the open end of the measuring cup 3. The swiping means 9 is movably attached to the frame part 1 for movement in a swiping path where a swiping member 10 of the swiping means 9 is configured to move essentially along the imaginary top wall at the open end of the measuring cup 3 so that the volume of the sample will have essentially the volume of the measuring cup 3. The swiping means 9 may be manually operable.

The measuring cup 3 is preferably, but not necessarily, supported by a scales means (not shown in the drawings) on the frame part 1 of the moisture meter. Said scales means may comprise a load cell 14 arranged between the frame part 1 of the moisture meter and the measuring cup 3 to measure the weight of the particulate material that has been poured into the measuring cup 3. The moisture meter may be arranged to indicate directly the bulk density of the sample of particulate material.

The moisture meter comprises preferably, but not necessarily, a temperature sensing element (not shown in the drawings) that has been arranged to project from the wall such as from the bottom wall 6 of the measuring cup 3 into the sample of particulate material that has been poured into the measuring cup 3.

The moisture comprises preferably, but not necessarily, a temperature sensing element which has been arranged to push from the wall such as from a cylindrical side wall 7 of the measuring cup 3 into the sample of particulate material that has been poured into the measuring cup 3.

In the moisture meter shown in the Figures, the swiping means 9 comprises two elongate members 11 pivotably attached at opposite sides of the frame part 1 and having said swiping member 10 arranged between said two elongate members for moving said swiping member 10 in said swiping path.

Figure 1:
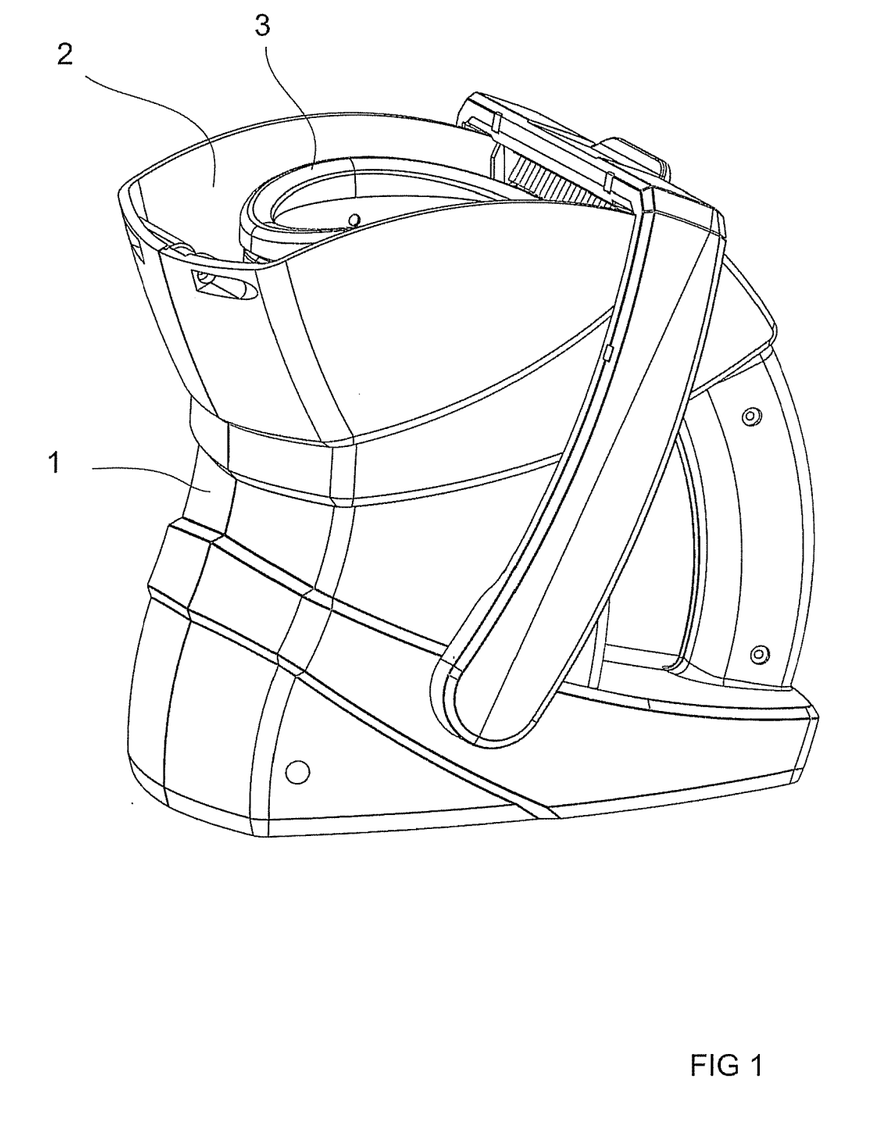
FIG. 1 shows an embodiment of the moisture meter.
Figure 2:
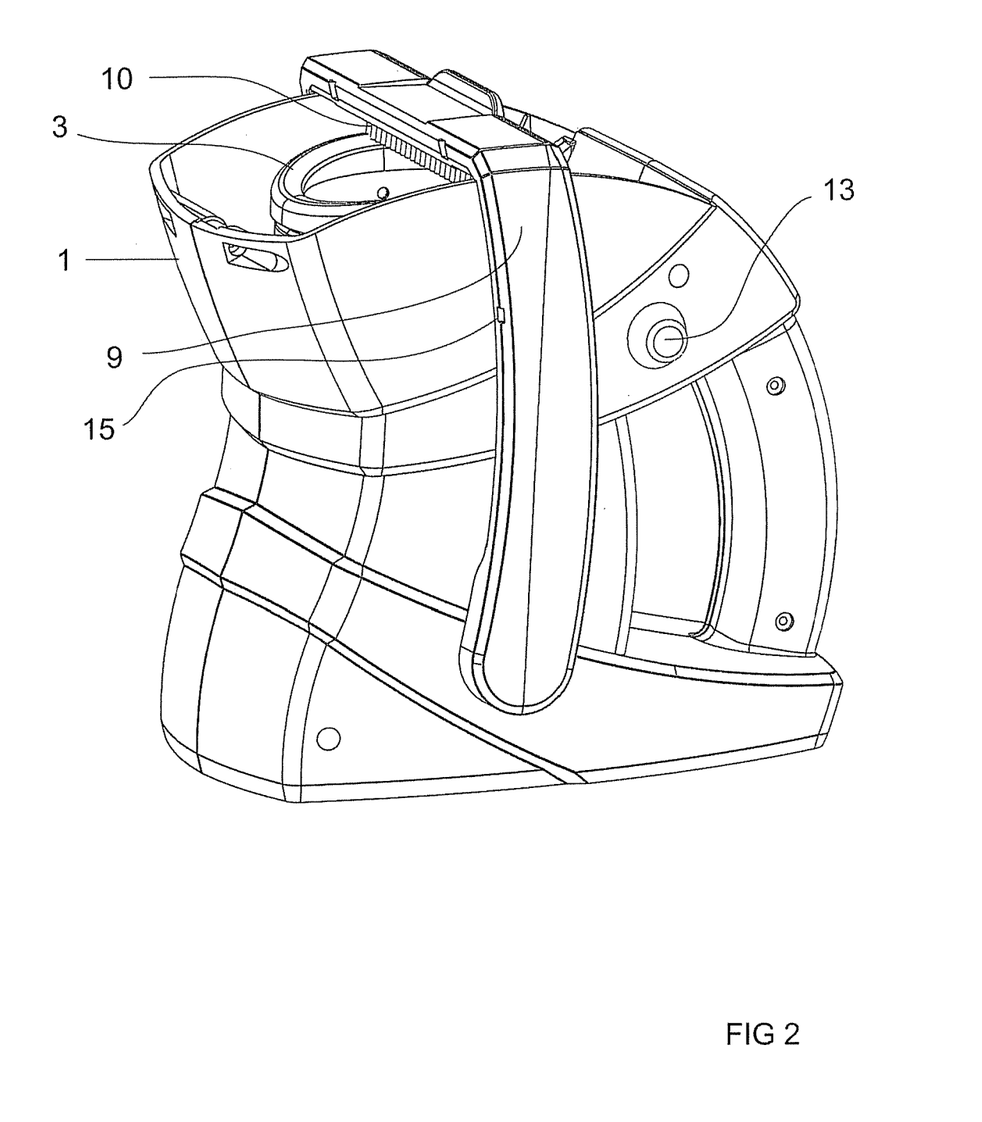
FIG. 2 shows the moisture meter shown in FIG. 1 in a stage where the swiping means have been moved along the open end of the measuring cup in the swiping path.
Figure 3:
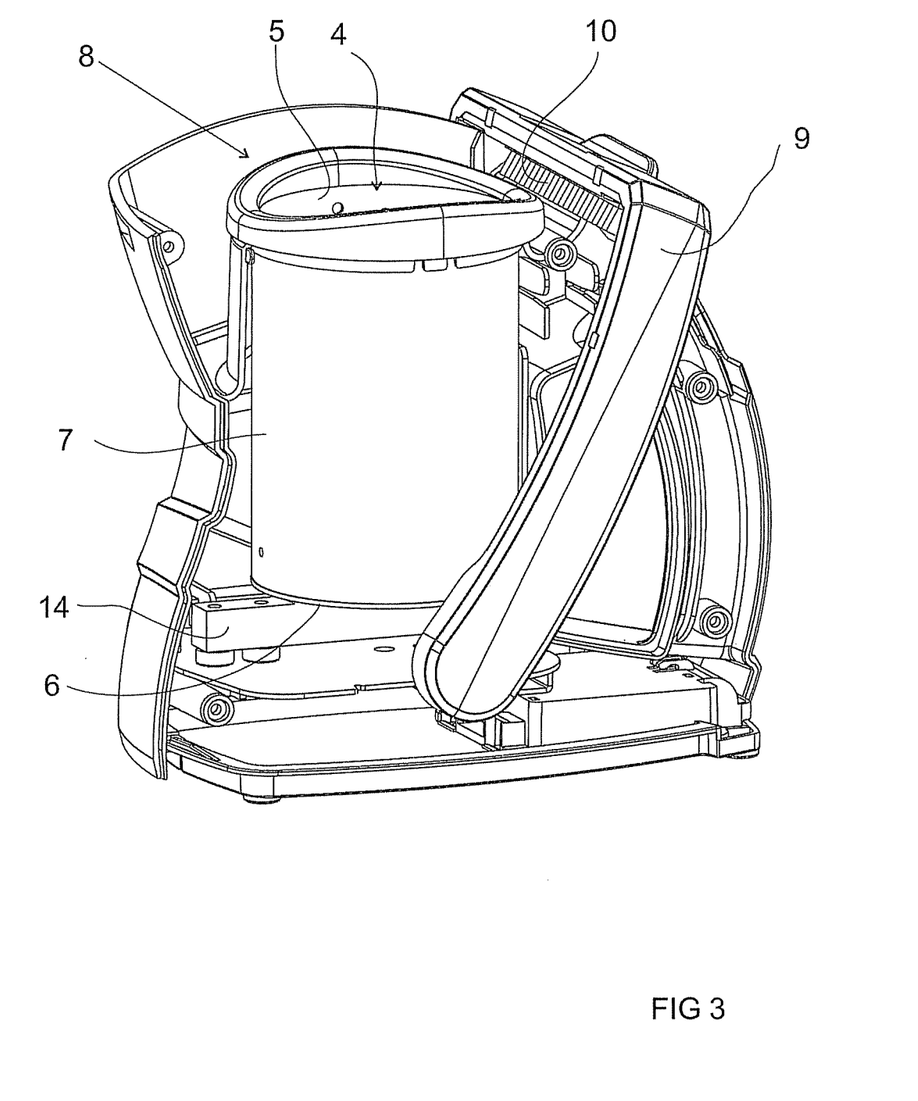
FIG. 3 shows the moisture meter shown in FIG. 1 in partly disassembled stage.
Figure 4:
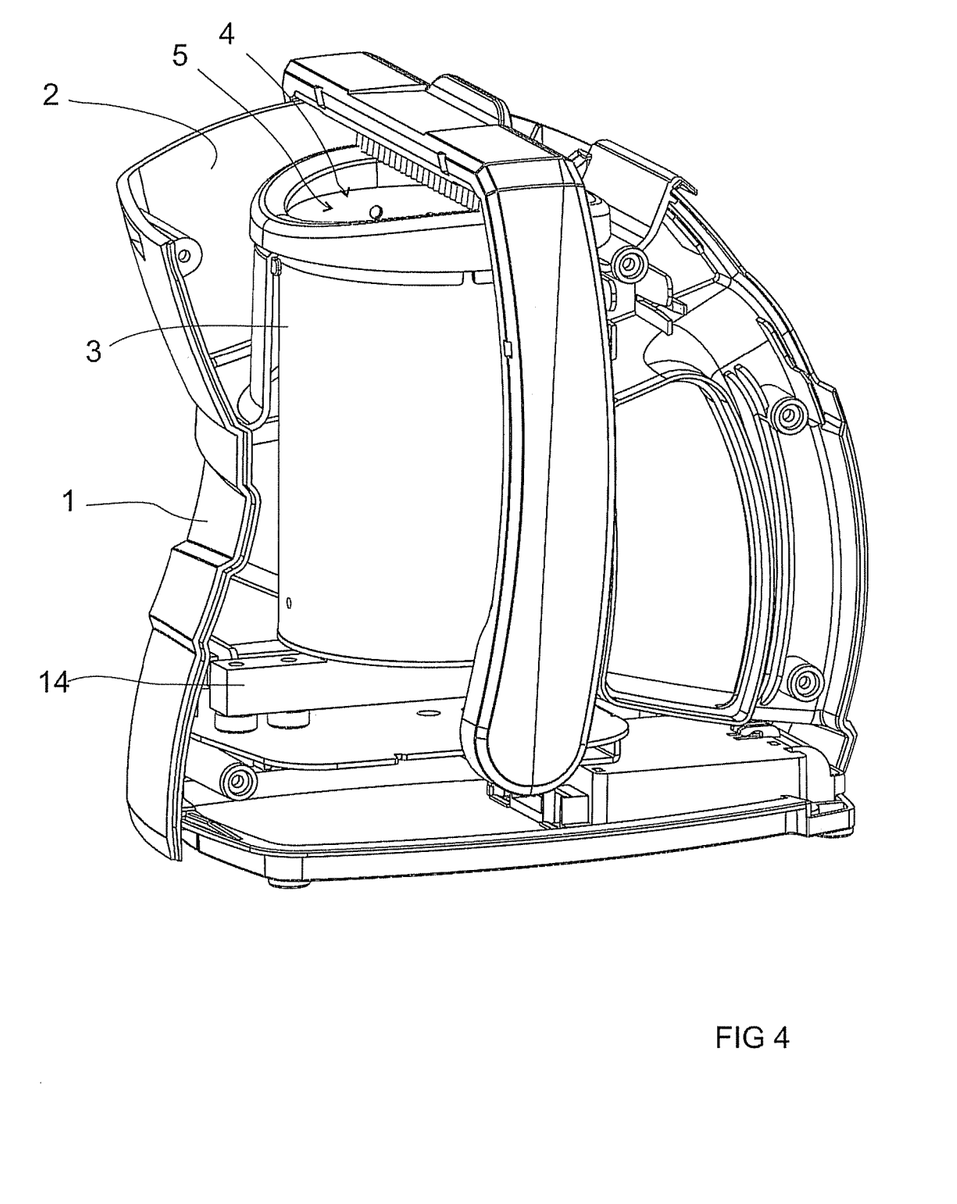
FIG. 4 shows the moisture meter shown in FIG. 3 in partly disassembled stage, where the swiping means have been moved along the open end of the measuring cup in the swiping path.
Figure 5:
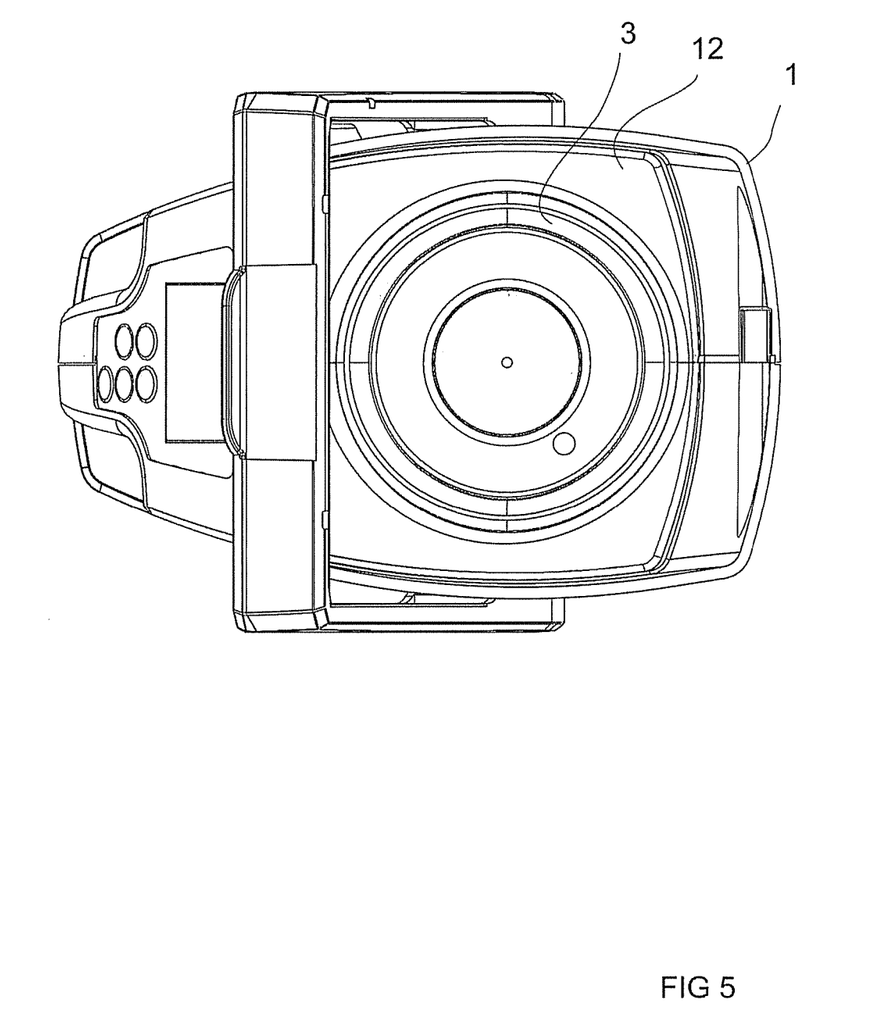
FIG. 5 shows the moisture meter shown in FIG. 1 as seen from above.
Figure 6:
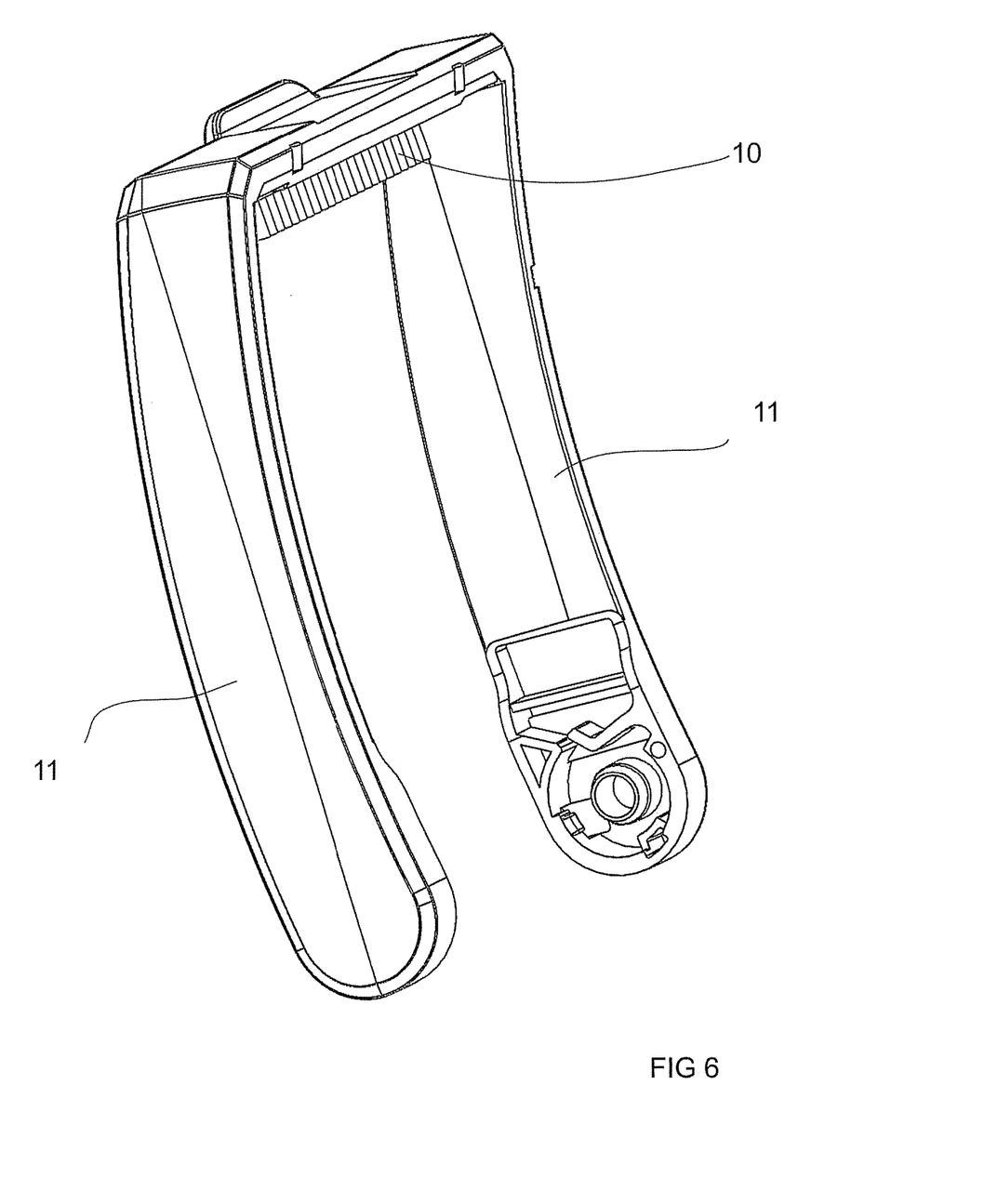
FIG. 6 shows the swiping means of the moisture meter shown in FIG. 1.

In the moisture meter shown in the Figures, the moisture meter is provided with a receiving vessel 12 at least partly, in FIG. 5 completely, surrounding the measuring cup 3 in the frame part 1 for receiving particulate material removed by the swiping means 9.

In the moisture meter shown in the Figures, the swiping means 9 is functionally connected to the moisture measuring means by a sensing means 13 sensing that the swiping member 10 has been moved at least partly in said swiping path along the opening of the measuring cup 3. In the moisture meter shown in the Figures, the sensing means 13 comprises a Hall effect sensor located within the frame part 1 and a magnet 15 located in the elongate member 11 of the swiping means 9.

In the moisture meter shown in the Figures, the swiping member 10 of the swiping means 9 is in the faun of a brush. The swiping member 10 of the swiping means 9 could alternatively comprise another form of flexible member or elastic member. Alternatively, the swiping means 9 can be made at least partly flexible or at least partly elastic. The purpose of the flexibility or the elasticity is to prevent large kernels, grains or similar from getting stuck during swiping.

In the moisture meter shown in the Figures, the measuring cup 3 has a cylindrical configuration.

The moisture meter is preferably, but not necessarily, a portable moisture meter.

While the present invention has been illustrated by the description of embodiments thereof and while the embodiments have been described in considerable detail, it is not the intention of the applicant to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and illustrative examples shown and described. Accordingly, departures may be made from such details without departing from the spirit or scope of the applicant's general inventive concept.

We claim:

1. A portable moisture meter for determining a moisture content of a particulate material, comprising:

a frame defining a frame space;

a first handle secured to the frame for holding the portable moisture meter;

a measuring cup disposed within the frame space for receiving a sample of the particulate material whose moisture content is to be measured, wherein the measuring cup comprises an open end through which the sample may be poured and an inner space having a measuring volume;

a moisture measuring means for measuring the moisture content of the sample received in the measuring cup; and a swiping member pivotably mounted to the frame and configured to move in a swiping path along the open end of the measuring cup, such that portions of the sample which are disposed outside of the inner space of the measuring cup are removed by the swiping member;

wherein the swiping member comprises a second handle member and a brush;

wherein the moisture of the sample is measured while the sample is in the cup and after the swiping member has removed portions of the sample which are disposed outside of the inner space of the measuring cup, two elongated members pivotably attached at opposite sides of the frame, and the swiping member extends between the two elongated members.

2. The moisture meter according to claim 1, wherein the moisture measuring means comprises a capacitor which corresponds to the measuring cup, and the moisture measuring means determines the moisture content of the sample at least in part by determining an impedance of the capacitor.

3. The moisture meter according to claim 1, wherein the moisture meter determines a bulk density of the sample of particulate material.

4. The moisture meter according to claim 1, further comprising a temperature sensor extending upwardly from a bottom of the measuring cup into the inner space as it contains the sample.

5. The moisture meter according to claim 1, further comprising a temperature sensor extending inwardly from a side wall of the measuring cup into the inner space as it contains the sample.

6. The moisture meter according to claim 1, wherein the measuring cup comprises a cylindrical configuration.

7. The moisture meter according to claim 1, further comprising a receiving vessel at least partly surrounding the measuring cup in the frame space for receiving particulate material removed by the swiping member.

8. The moisture meter according to claim 1, wherein the swiping member is manually operable.

9. The moisture meter according to claim 1, wherein the moisture meter is a portable moisture meter.

10. The moisture meter according to claim 1, further comprising a scale disposed in the frame space underneath the measuring cup to determine a weight of the measuring cup as it contains the sample.

11. The moisture meter according to claim 10, wherein the scale comprises a load cell.

12. The moisture meter according to claim 1, further comprising a sensor which determines that the swiping member has been moved at least partly along the sweeping path.

13. The moisture meter according to claim 12, wherein the sensor comprises a Hall effect sensor disposed on the frame to detect a magnet that moves with the swiping member.

14. A moisture meter for determining a moisture content of a particulate material, comprising:
- a frame defining a frame space;
- a measuring cup disposed within the frame space for receiving a sample of the particulate material whose moisture content is to be measured, wherein the measuring cup comprises an open end through which the sample may be poured and an inner space having a measuring volume;
- a moisture measuring means for measuring the moisture content of the sample received in the measuring cup;
- a swiping member configured to move in a swiping path along the open end of the measuring cup, such that portions of the sample which are disposed outside of the inner space of the measuring cup are removed by the swiping member; and
- two elongated members pivotably attached at opposite sides of the frame, and the swiping member extends between the two elongated members;
- wherein the moisture of the sample is measured while the sample is in the cup and after the swiping member has removed portions of the sample which are disposed outside of the inner space of the measuring cup, a first handle secured to the frame for holding the portable moisture meter.

15. A portable moisture meter for determining a moisture content of a particulate material, comprising:
- a frame defining a frame space;
- a first handle secured to the frame for holding the portable moisture meter;
- a measuring cup disposed within the frame space for receiving a sample of the particulate material whose moisture content is to be measured, wherein the measuring cup comprises an open end through which the sample may be poured and an inner space having a measuring volume;
- a moisture measuring means for measuring the moisture content of the sample received in the measuring cup; and
- a swiping member pivotably mounted to the frame and configured to move in a swiping path along the open end of the measuring cup, such that portions of the sample which are disposed outside of the inner space of the measuring cup are removed by the swiping member;
- wherein the swiping member comprises an elastic member;
- wherein the moisture of the sample is measured while the sample is in the cup and after the swiping member has removed portions of the sample which are disposed outside of the inner space of the measuring cup, two elongated members pivotably attached at opposite sides of the frame, and the swiping member extends between the two elongated members.

16. The moisture meter according to claim 15, wherein the moisture measuring means comprises a capacitor which corresponds to the measuring cup, and the moisture measuring means determines the moisture content of the sample at least in part by determining an impedance of the capacitor.

17. The moisture meter according to claim 15, further comprising two elongated members pivotably attached at opposite sides of the frame, and the swiping member extends between the two elongated members.

18. The moisture meter according to claim 15, wherein the swiping member is manually operable.

19. The moisture meter according to claim 15, further comprising a sensor which determines that the swiping member has been moved at least partly along the sweeping path.

20. The moisture meter according to claim 19, wherein the sensor comprises a Hall effect sensor disposed on the frame to detect a magnet that moves with the swiping member.

* * * * *